US007796727B1

(12) United States Patent
Kaufman

(10) Patent No.: US 7,796,727 B1
(45) Date of Patent: Sep. 14, 2010

(54) AEROSOL CHARGE CONDITIONER

(75) Inventor: Stanley L. Kaufman, New Brighton, MN (US)

(73) Assignee: TSI, Incorporated, Shoreview, MN (US)

(*) Notice: Subject to any disclaimer, the term of this patent is extended or adjusted under 35 U.S.C. 154(b) by 0 days.

(21) Appl. No.: 12/411,240

(22) Filed: Mar. 25, 2009

Related U.S. Application Data

(60) Provisional application No. 61/070,880, filed on Mar. 26, 2008.

(51) Int. Cl.
*G21K 5/00* (2006.01)
*G21K 5/08* (2006.01)

(52) U.S. Cl. .......................................... 378/64; 378/66

(58) Field of Classification Search .................. 378/64, 378/66; 250/282; 361/231, 213; 422/186.04, 422/121

See application file for complete search history.

(56) References Cited

U.S. PATENT DOCUMENTS

| | | | |
|---|---|---|---|
| 4,701,379 A | 10/1987 | Pearson et al. | |
| 4,701,941 A | 10/1987 | Szirmai et al. | |
| 4,827,371 A | 5/1989 | Yost | |
| 5,254,229 A | 10/1993 | Ohmi et al. | |
| 5,596,478 A | 1/1997 | Ohmi et al. | |
| 5,621,605 A | 4/1997 | Inaba et al. | |
| 5,750,011 A | 5/1998 | Ohmi et al. | |
| 5,883,934 A | 3/1999 | Umeda | |
| 5,949,849 A | 9/1999 | Hirano et al. | |
| 6,429,426 B1 | 8/2002 | Doring | |
| 6,563,110 B1 * | 5/2003 | Leri | 250/282 |
| 6,861,036 B2 * | 3/2005 | Biswas et al. | 422/186.04 |
| 7,397,647 B2 | 7/2008 | Mizuno et al. | |
| 7,522,703 B2 | 4/2009 | Okuyama et al. | |
| 7,660,097 B2 | 2/2010 | Lee | |
| 2006/0098778 A1 | 5/2006 | Oettinger et al. | |
| 2006/0108537 A1 | 5/2006 | Okuyama et al. | |

FOREIGN PATENT DOCUMENTS

| | | |
|---|---|---|
| EP | 1 542 238 | 6/2005 |
| JP | 2002 208031 | 7/2002 |
| KR | 1020050028028 | 4/2005 |

OTHER PUBLICATIONS

Kanomax, Soft X-ray Aerosol Charger, New York, NY, Osaka Japan.
Lee et al., "Bipolar diffusion charging for aerosol nanoparticle measurement using a soft X-ray charger," Journal of Aerosol Science, (2005) vol. 36, pp. 813-829.

(Continued)

*Primary Examiner*—Irakli Kiknadze
(74) *Attorney, Agent, or Firm*—Patterson Thuente Christensen Pedersen, P.A.

(57) ABSTRACT

An attenuated soft x-ray neutralizer for neutralizing aerosols. The apparatus includes a soft x-ray emitter that emits soft x-rays into an aerosol conditioning chamber. An attenuating window may be included that reduces the intensity of the soft x-rays that bombard the aerosol, thus generating fewer radiolytically generated particles. Another way to reduce or control the intensity of the soft x-rays is to control emission of the cathode in the soft x-ray emitter. The reduced intensity of the soft x-rays was found by experiment to satisfactorily condition an aerosol stream without substantial radiolytic generation of particles precipitation.

20 Claims, 6 Drawing Sheets

OTHER PUBLICATIONS

Shimada et al., "Bipolar Charging of Aerosol Nanoparticles by a Soft X-ray Photoionizer," Journal of Chemican Engineering of Japan, (2002) vol. 35, No. 8, pp. 786-793.

Yun et al., "Effect of X-ray energy and ionization time on the charging performance and nanoparticle formation of a soft X-ray photoionization charger," Advanced Powder Technology, vol. 20 (2009) pp. 529-536.

Han et al., "Generation of Singly Charged Aerosol Particles Using a Power Adjustable Soft X-Ray Charger," (2004), pp. 1-2, Korea.

Han et al, "Unipolar Charging of Nanosized Aerosol Particles Using Soft X-ray Photoionization," Aerosol Science and Technology, (2003), pp. 330-341.

Hogan et al., "Capture of Viral Particles n Soft S-Ray Enhanced Corona Systems: Charge Distribution and Transport Characteristics," Aerosol Science and Technology, (2004), pp. 475-486.

Hogan et al., "Nanoparticle Capture in the 6-15nm Size Range Utilizing Direct Soft X-ray Photoionization and Diffusion Charging: Theory and Experiments," Aerosol Physics, (2006), pp. 690-691.

Kulkarni et al., "Charging of particles in unipolar coronas irradiated by in-situ soft X-rays: enhancement of capture efficiency of ultrafine particles," Journal of Aerosol Science, Taipei, Taiwan, pp. 1279-1296 (2002),.

Shimada et al., "Charging of Nanosized Aerosol Particles by Soft X-Ray Photoionization," International Symposium on Nanoparticles: Technology and Sustainable Development, pp. 85-87 (2002).

Kanomax, "Soft X-ray Aerosol Charger," New York, NY, Osaka Japan, published prior to Mar. 26, 2008.

Wiedensholer, "An approximation of the bipolar charge distribution for particles in the submicron size range," J. Aerosol Sci, vol. 19, No. 3, pp. 387-389 (1988).

* cited by examiner

Description
AEROSOL CHARGE CONDITIONER

RELATED APPLICATIONS

This Application claims the benefit of U.S. Patent Application No. 61/070,880, filed Mar. 26, 2008, which is hereby incorporated by reference in its entirety.

BACKGROUND OF THE INVENTION

Aerosol neutralizers are utilized in a variety of aerosol application and test devices, including characterization of aerosols that are sparsely populated (e.g. the monitoring of clean room environments) as well as aerosols that are particle laden (e.g. combustion engine exhaust, coating sprays). The primary task of the aerosol neutralizer is to condition the aerosol to obtain a reproducible, steady-state population of particles having a distribution of charged (positive and negative) particles and neutral particles that is known to within an acceptable uncertainty, and to produce such a characteristic in the aerosol regardless of the charge condition of the aerosol entering the aerosol neutralizer. By conditioning the aerosol to a known steady-state population, the total concentration of particles can be inferred by measuring only a portion of the particle distribution (e.g., particles of a certain size, mobility, and/or charge).

For example, some detectors detect only positively charged particles within a given size range. Because the steady state population of particles is reasonably known relative to the positively charged particles within the size range, the total concentration of the particles can be inferred. An unconditioned aerosol stream may not possess the steady state characteristics, thus rendering the inference meaningless.

One way to condition an aerosol is to bombard it with x-rays. The x-rays interact with the gas in the aerosol, producing a bi-polar population of ions. These ions then interact with the particles of the aerosol, thereby transferring charge to the particles. Particles having a high charge upon entering the aerosol neutralizer will attract oppositely charge ions generated in the gas, thus tending to neutralize the particle. By this same mechanism, most of the smaller particles will not sustain multiple charges of a given polarity. Larger particles can sustain multiple charges by virtue of their size. See Wiedensohler, "An Approximation of the Bipolar Charge Distribution for Particles in the Submicron Size Range," J. Aerosol Sci., vol. 19, no. 3, pp. 387-389, 1988. Accordingly, the steady state distribution of the aerosol population comprising a mixture of neutral particles, single-charged particles and multiple-charged particles is rapidly attained under x-ray bombardment.

Conventional neutralizing devices utilizing radioactive substances such as americium ($^{241}$Am), krypton ($^{85}$Kr), polonium ($^{210}$Po) and the like are known to produce a bipolar population of charged particles in an aerosol. Such devices carry with them concerns stemming from the hazardous radiation attendant the radioactive substance and from the gradual decrease of effectiveness characterized by the half-life. Americum has a half-life of 432 years and krypton a half-life of 11 years, thus posing safety concerns both in terms of personnel utilizing and storing the device, and in terms of disposal of the unit when its operational life is at an end. Polonium has a substantially shorter half life (138 days), which may mitigate against long term disposal concerns, but presents additional handling concerns as the radioactive substance typically requires replacement during the operational life of the neutralizer.

Recently, U.S. Patent Application Publication No. 2006/0108537 disclosed an aerosol particle charging device that utilizes "soft" x-rays, that is, x-rays having a wavelength in the range of approximately 0.13- to 2-nm and having photon energies in the range of approximately 600- to 10,000-electron-volts (eV). Soft x-ray devices eliminate concerns regarding handling of radioactive materials because the soft x-ray emitter does not utilize or produce radioactive materials nor does it emit any radiation when no power is supplied to it.

However, both the conventional and the soft x-ray devices are known to generate particles by a process of radiolytic precipitation. Radiolytic precipitation is the result of a cascade of events beginning with ionization of individual molecules which form reactive species from gas constituents and impurities in an aerosol, subsequently interacting with each other to condense into particles. Hence, aerosol neutralizers utilizing x-ray devices typically add particles to an aerosol stream via radiolytically produced particle. The generated particles are generally undesirable, as they typically add particles of unknown size and composition to an aerosol, thereby distorting the aerosol that is being characterized.

A neutralizer that provides the radioactivity-free operation of the soft x-ray emitter without significant radiolytic generation of particles would be welcome.

SUMMARY OF THE INVENTION

Various embodiments of the invention reduce the radiolytic generation of particles to a negligible amount while still fully conditioning an aerosol stream, even at high flow rates. The reduction in the radiolytic generation of particles is accomplished by reducing by several factors the intensity of the soft x-rays that bombard the aerosol flow being conditioned. We have found that the reduction in radiolytically generated particles drops exponentially in relation to the decrease in the intensity of the soft x-rays, while the reduction in the production of the bi-polar population in ions is only modestly reduced. The result is that the radiolytic generation of particles is disproportionately diminished relative to the reduction in the generation the of bi-polar population of ions. Furthermore, we have discovered that in some instances the intensity of a standard soft x-ray emitter can be reduced by as much as a factor of 33 times and still produce a bi-polar population of ions sufficient to neutralize an aerosol.

Structurally, a soft x-ray emitter is configured to irradiate an aerosol conditioning chamber through which an aerosol passes. An attenuating window may be positioned between the soft x-ray emitter and the interior passage of the aerosol conditioning chamber so that the soft x-rays passing therebetween pass through the attenuating window. Through proper selection of material and thickness, the intensity of the soft x-rays that irradiate the aerosol flow can strike a balance whereby the radiolytic generation of particles is insignificant for a given application while the conditioning of the aerosol flow is still complete.

In one embodiment, an aerosol conditioning device comprises an aerosol conditioning chamber having an inlet and an outlet and defining an interior flow passage. A soft x-ray emitter is operatively coupled with the aerosol conditioning chamber, with an attenuating window disposed between the soft x-ray emitter and the interior flow passage. The attenuating window may be adapted to reduce the intensity of soft x-rays emitted by the soft x-ray emitter so that radiolytically generated particles produced by the soft x-rays within the interior flow passage is insignificant. The attenuating window may be configured to reduce the intensity of soft x-rays emitted by the soft x-ray emitter by a factor of approximately 33.

The soft x-rays entering the aerosol conditioning chamber may be tailored to produce an x-ray intensity of approximately 0.045 Sievert/hour or less, depending on the sensitivity of the downstream measurements to radiolytically generated particles.

In another embodiment, a method for neutralizing an aerosol while generating an insignificant amount of radiolytically generated particles comprises providing a soft x-ray emitter operatively coupled with an aerosol conditioning chamber defining an interior flow passage, the soft x-ray emitter being configured to produce soft x-rays of a rated intensity. The x-ray emitter is then caused to emit soft x-rays. The intensity of the soft x-rays produced by the soft x-ray emitter is reduced to provide soft x-rays of a reduced intensity relative to the rated intensity. At least a portion of the reduced intensity soft x-rays is caused to enter the aerosol conditioning chamber and to pass through the conditioning chamber. The aerosol is thereby bombarded with the soft x-rays of reduced intensity as the aerosol passes through the conditioning chamber to generate an insignificant number of radiolytically generated particles.

DETAILED DESCRIPTION OF THE DRAWINGS

Figure 1:
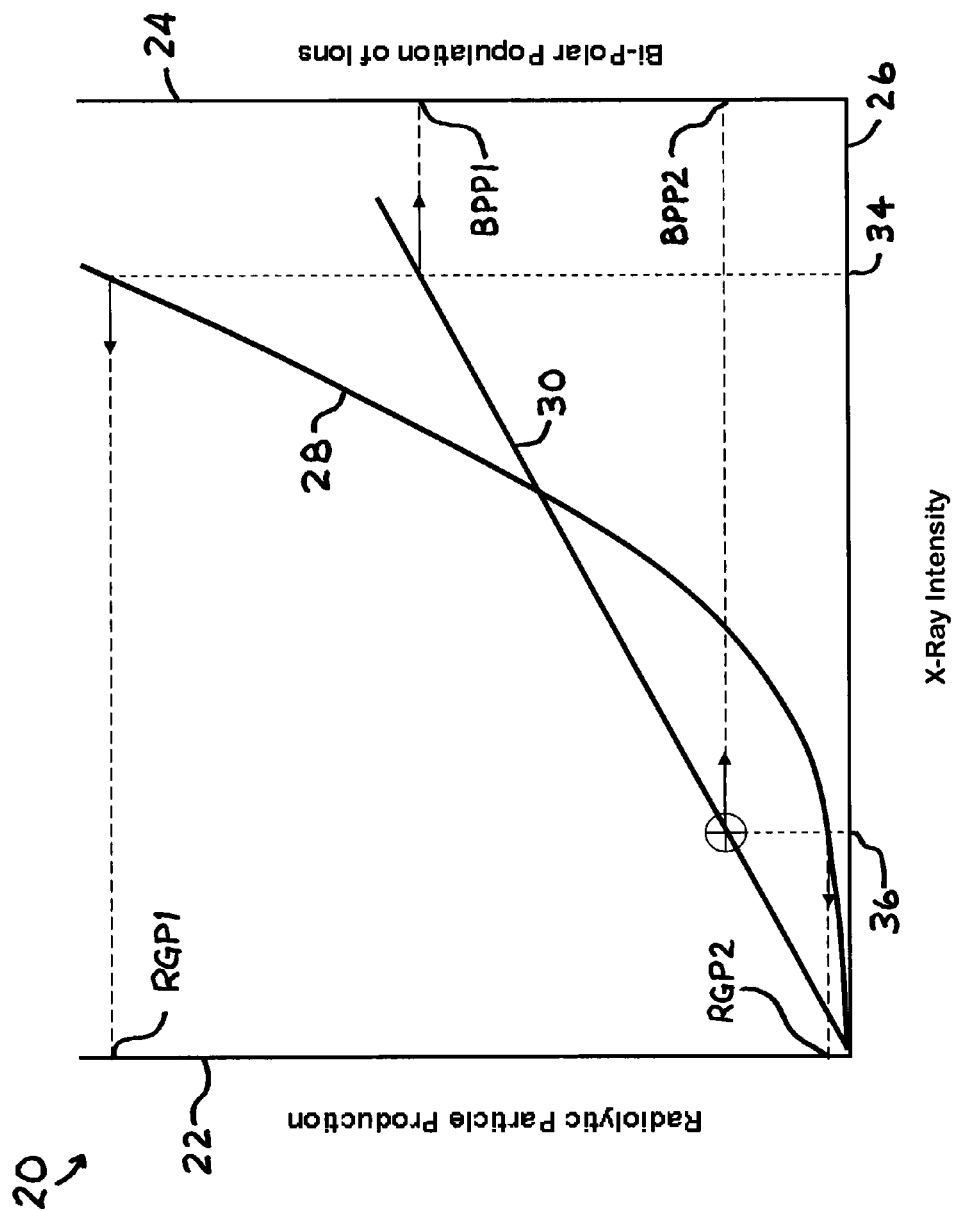
FIG. 1 is a trend graph of radiolytic generation of particles and bi-polar population of ions vs. x-ray intensity.

Referring to FIG. 1, a dual ordinate graph 20 having a radiolytically generated particle ordinate 22 and a bi-polar population of ions ordinate 24 vs. an x-ray intensity abscissa 26 is presented. A radiolytic production characteristic 28 and a bi-polar population characteristic 30 as generated by soft x-rays are depicted on the dual ordinate graph 20.

The radiolytic production characteristic 28 is generally proportional to the x-ray intensity abscissa 26 raised to a power M, i.e.

$$RGP \propto X^M \qquad \text{Eqn. (1)}$$

where RGP is the radiolytically generated production rate, X is the x-ray intensity, and M is a value greater than unity and believed to be typically greater than 2.

The bi-polar population characteristic 30 may range from approximately a square root function to approximately a linear function with respect to the x-ray intensity abscissa 26:

$$BPP \propto X^N \qquad \text{Eqn. (2)}$$

where BPP is the bi-polar population at x-ray intensity X and N is in the range of approximately ½ to 1.

A full power x-ray intensity level 34 for a typical soft x-ray emitter is depicted on the x-ray intensity abscissa 26, at which level the radiolytic production characteristic 28 is at a first value RGP1 and the bi-polar population characteristic 30 is at a first value BPP1.

Typically, BPP1 is substantially greater than is required to adequately condition an aerosol flow through a neutralizer. Moreover, because the power M of the radiolytic production characteristic 28 typically greater than two and the bi-polar population characteristic 30 is approximately linear or sub-linear, the value of the RGP will decrease in greater proportion than will the value of the BPP as the x-ray intensity X is decreased.

Accordingly, an adequate x-ray intensity level 36 may be established that is less than the full power x-ray intensity level 34, where the bi-polar population characteristic 30 is at a second value BPP2. A corresponding value RGP2 of the radiolytic production characteristic 28 is also established at the adequate x-ray intensity level 36. The dual ordinate graph 20 illustrates that the proportionate change between RGP1 and RGP2 is substantially greater than the proportionate change between BPP1 and BPP2. Therefore, while the bi-polar population of ions 24 remains adequate, the radiolytically generated particle production may become insignificant or marginal in terms of the contribution of particles to the aerosol being conditioned.

Figure 2:
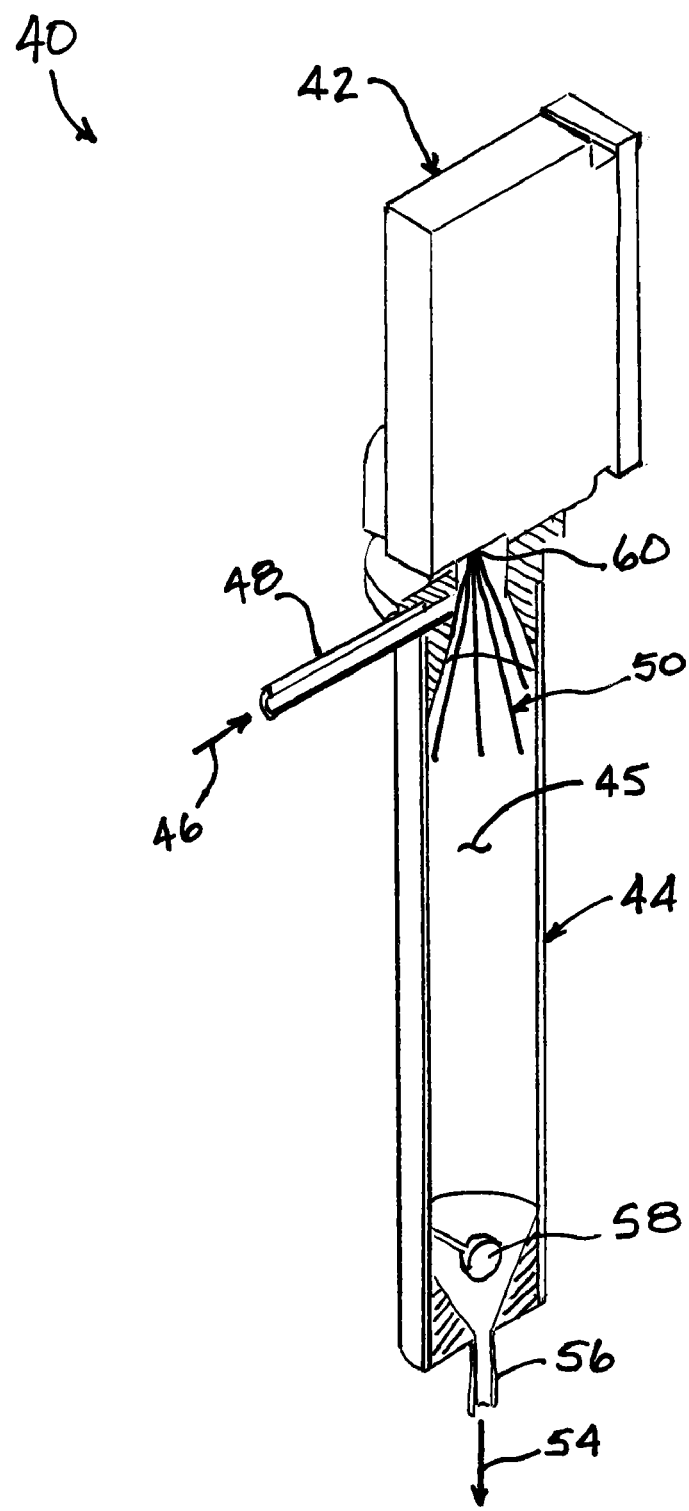
FIG. 2 is a cut-away view of a soft x-ray neutralizer in an embodiment of the invention.
Figure 3:
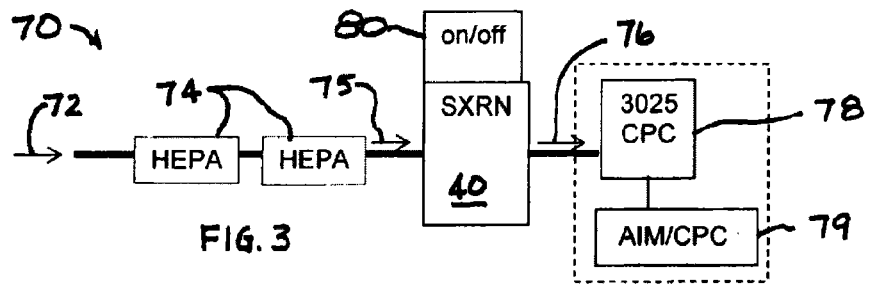
FIG. 3 is a block diagram of a particle generation test setup.
Figure 4:
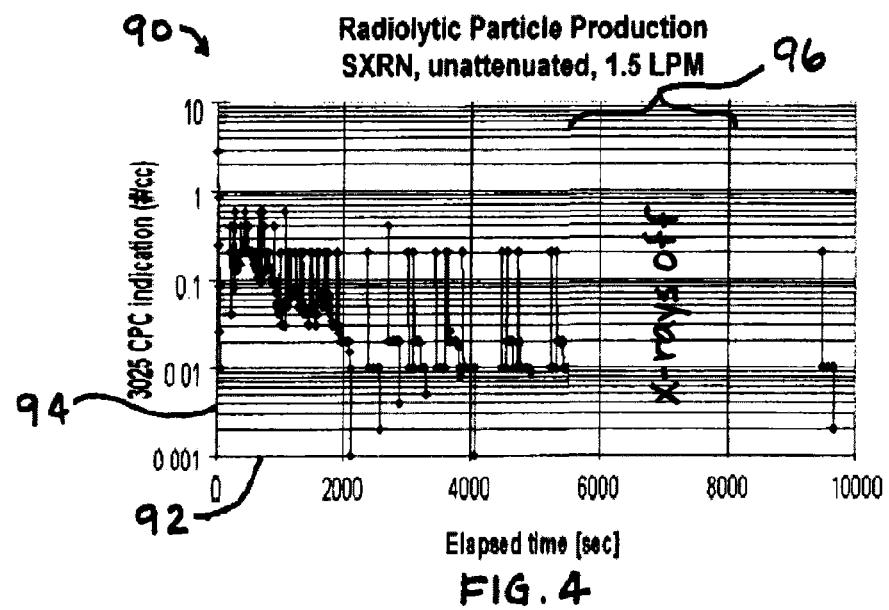
FIG. 4 is a graph of the particle production test for an unattenuated soft x-ray neutralizer at a flow rate of 1.5 liters per minute.
Figure 5:
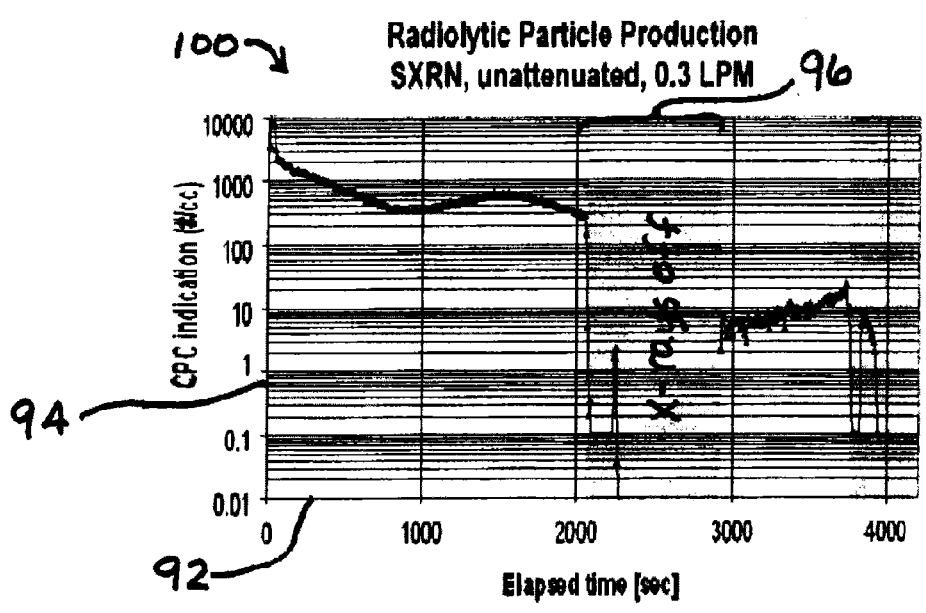
FIG. 5 is a graph of the particle production test for an unattenuated soft x-ray neutralizer at a flow rate of 0.3 liters per minute.
Figure 6:
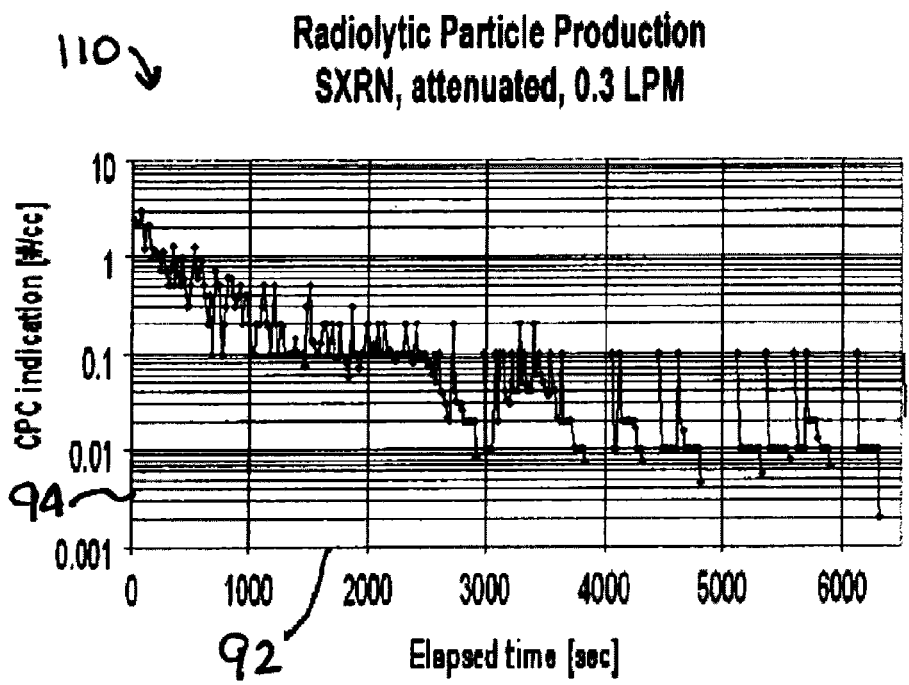
FIGS. 6 and 6A are graphs of the results from the particle production test for an attenuated soft x-ray neutralizer at a flow rate of 0.3 liters per minute.
Figure 6A:
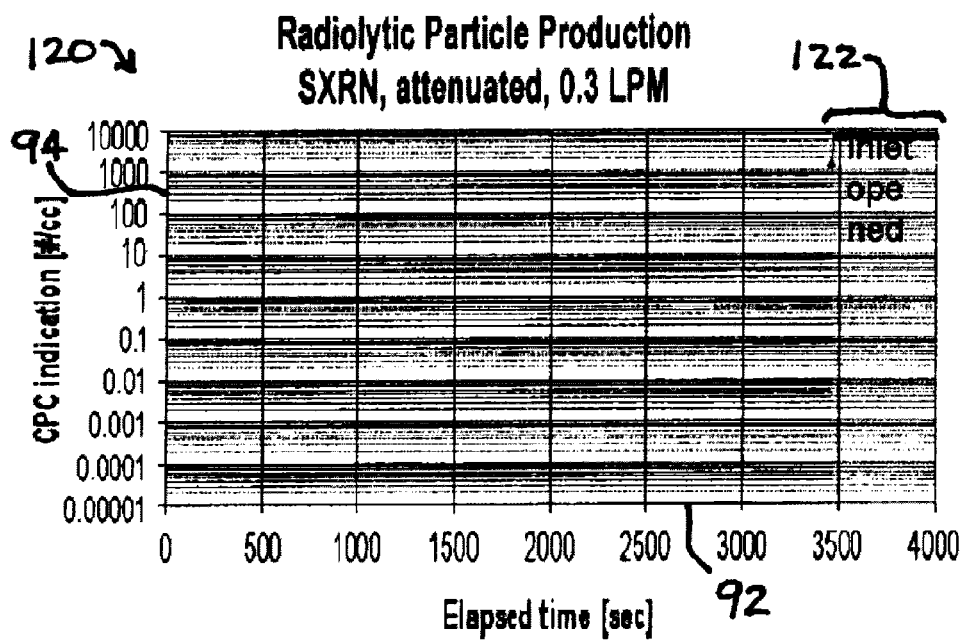

Referring to FIG. 2, a soft x-ray neutralizer (SXRN) 40 is depicted in an embodiment of the invention. The soft x-ray neutralizer 40 includes a soft x-ray emitter 42 operatively coupled with an aerosol conditioning chamber 44 that defines an interior flow passage 45. An unconditioned aerosol 46 may be introduced into the interior flow passage 45 through a first port 48. Soft x-rays 50 are emitted from the soft x-ray emitter 42 and directed into the interior flow passage 45 of the aerosol conditioning chamber 44. A conditioned aerosol 54 emerges from the aerosol conditioning chamber 44 via a second port 56. An obstruction 58 such as a sphere or perforated plate may be placed upstream of the second port 56. An attenuating window 60 may be placed between the soft x-ray emitter 42 and the interior of the aerosol conditioning chamber 44.

Alternatively, the flow of aerosol may be reversed. That is, the unconditioned aerosol 46 may enter the second port 56 and the conditioned aerosol 54 exit via port 48. Because the bi-polar population of ions tends to be more concentrated near the soft x-ray emitter, the reversed flow configuration may change the residence time of the bi-polar population of ions within the aerosol conditioning chamber 44. The change in residence time of the ions can be a factor in the radiolytic generation of particles.

In operation, the unconditioned aerosol 46 may be bombarded with soft x-rays 50 emitted from the soft x-ray emitter 42 as the aerosol passes through the aerosol conditioning chamber 44. The soft x-rays 50 interact with the carrier gas of the aerosol to generate ions, which in turn can interact with the particles in the aerosol to transfer charges to the particles. The attenuating window 60 may form a fluid flow barrier between the internal components of the soft x-ray emitter 42 and the aerosol conditioning chamber 44.

The obstruction 58 blocks the direct line-of-sight between the attenuating window 60 and the second port 56 for enhanced safety of personnel in the area. Alternatively, the blocking function may also be accomplished by imposing a bend or turn or serpentine in the structure that defines the second port 56.

The attenuating window 60 may be comprised of a material and thickness that substantially reduces the intensity of the soft x-rays 50 that enter the aerosol conditioning chamber 44.

The attenuation may be tailored so that the intensity of the soft x-rays 50 is adequate to condition the unconditioned aerosol 46 as it flows through the aerosol conditioning chamber 44, as described in the discussion of FIG. 1. The reduced intensity of the soft x-rays 50 also provides the attendant and disproportionately larger reduction in the production of radiolytically generated particles.

Experiments were devised and executed to determine the feasibility of the foregoing method and apparatus. The experiments and results are described below.

Referring to FIG. 3, a particle generation test setup 70 was devised to test whether the soft x-ray neutralizer 40, either attenuated or unattentuated, produced radiolytically generated particles. For the tests under discussion, the "unattenuated" configuration of the soft x-ray neutralizer comprised a window of mylar of 0.004-in. thickness. In the "attenuated" configuration, the window 60 further included multiple layers of aluminum foil totaling 0.005-in. thickness. (The attenuation provided is a function of the total thickness of material, not the number of layers.) The attenuated configuration was found to reduce the intensity of the soft x-rays entering the aerosol neutralizing chamber 44 by a factor of approximately thirty-three (i.e. from approximately 1.5 Sievert/hour to approximately 0.045 Sievert/hour). The intensity of the soft x-rays entering the neutralizing chamber 44 was estimated by interpolating the specifications of the soft x-ray emitter 42. The soft x-ray emitter 42 used in the particle generation test setup 70 was a Hamamatsu L9490, which specifies an x-ray dose at a distance of one meter from the output window of the device of 0.015 Sievert/hour. The midpoint of the neutralizing chamber 44 was approximately 10-cm from the output window. Because radiation intensity varies by the inverse of the distance squared, the dose at 10-cm will be approximately 100 times greater than at 1-m, putting the dose at about 15 Sievert/hour without attenuation. For an attenuation factor of 33, the attenuated x-ray intensity for the particle generation test setup 70 was therefore approximately 0.045 Sievert/hour.

The SI unit of radiation dose is the Gray, which is the amount of radiation that deposits 1 Joule in a kilogram of absorbing material. The Sievert is the Gray dosage multiplied by a factor that includes damage to biological tissue. For example, penetrating ionizing radiation (e.g., gamma and beta radiation) have a factor of about 1, so 1 Sievert=approximately 1 Gray. Alpha rays have a factor of 20, so 1 Gray of alpha radiation dosage=20 Sievert.

The soft x-ray neutralizer 40 was configured so that an unconditioned atmospheric flow stream 72 was drawn through a pair of high efficiency particulate air (HEPA) filters 74 connected in series in order to remove substantially all particles from the flow stream and produce a clean air flow 75 that enters the soft x-ray neutralizer 40. An exit flow 76 from the soft x-ray neutralizer 40 was directed into a condensation particle counter 78 (TSI model 3025) and processing software 79 (TSI Aerosol Instrument Manager Software for CPC). The soft x-ray neutralizer 40 was operatively coupled to an on/off control 80. It is further noted that the soft x-ray neutralizer 40 was configured for reverse flow in the particle generation test setup 70 (aerosol entering port 56 and exiting first port 48).

In operation, the soft x-ray neutralizer 40 could either be in an inactive state (i.e. controller 80 off) or an active state (i.e. controller 80 on). With the soft x-ray neutralizer 40 in the inactive state, the condensation particle counter 78 measures only the particles that pass thorough the pair of HEPA filters 74. With the soft x-ray neutralizer in the active state, the particles detected by the condensation particle counter 78 would be the combination of what passed through the HEPA filters 74 and the particles radiolytically generated by the soft x-ray neutralizer 40 in operation. Because of the extensive filtration, it was expected that the amount of particles detected by the condensation particle counter 78 would be very low with the soft x-ray neutralizer 40 in the inactive state, and that the particles detected by the condensation particle counter 78 would comprise substantially only the particles produced radiolytically by the soft x-ray neutralizer 40 in the active state.

Referring to FIGS. 4 through 6, the results of the particle generation test are presented. A high flow rate result 90 is presented in FIG. 4, wherein the particle generation test setup 70 was adjusted to draw 1.5 liters per minute (LPM) of air therethrough. During this test, the soft x-ray neutralizer was active and in an unattenuated configuration (that is, with the mylar window of 0.004-in. thickness between the x-ray emitter 42 and the aerosol conditioning chamber 44). The graph of FIG. 4 plots an elapsed time 92 of the experiment vs. the overall particle concentration 94 indicated by the condensation particle counter 78 on a logarithmic axis. An interval of inactivity 96 is also presented in FIG. 4, wherein the soft x-ray neutralizer 40 was in an inactive state.

The high flow rate results 90 indicate overall particle concentrations detectable by the condensation particle counter to be largely in the range of 0.01- to 1.0-particles per cubic centimeters (#/cc). No detectable particles were found during the interval of inactivity 96, implying that the particles detected during the high flow rate experiment are purely radiolytically generated particles. Generally, a radiolytically generated particle contribution of 1.0#/cc or less is considered satisfactory in many applications.

A low flow rate result 100 is presented in FIG. 5, wherein the particle generation test setup 70 was adjusted to draw 0.3 liters per minute (LPM) of air therethrough. As with the high flow rate result 90, the low flow rate result 100 was generated using an unattenuated soft x-ray neutralizer 40, and is characterized by a period of inactivity.

The low flow rate results 100 indicate overall particle concentrations detectable by the condensation particle counter to be initially in the range of 200 to 2000#/cc, and dropping to approximately 10#/cc after the period of inactivity 96. The detectable level of particles found during the interval of inactivity 96 was on the order of 0.1#/cc, which is two to four orders of magnitude less than the concentration measurements acquired in the active state; hence, the contribution of non-radiolytic particles can be presumed negligible. The substantially higher particle concentrations for the low flow rate results 100 may be problematic in many applications.

Second low flow rate results 110 and 120 are presented in FIGS. 6 and 6A, wherein the soft x-ray neutralizer 40 was arranged for the attenuated configuration. The low flow rate of 0.3 LPM was chosen because of the potentially problematic result demonstrated with the low flow rate result 100.

The initial second low flow rate result 110 presents data that was acquired over a period of approximately 2 hours. Initially, the production of radiolytically generated particles was approximately 2#/cc, rapidly decreasing to approximately 0.1#/cc, then steadily decreasing into approximately 0.01#/cc. Accordingly, the second low flow rate results 110 may be characterized as demonstrating that the attenuated configuration produces radiolytically generated particle concentrations that are typically less than 1#/cc, which constitutes a decrease in the production of radiolytically generated particles of over three orders of magnitude in some instances over the non-attenuated counterpart of the low flow rate results 100.

After the initial second flow rate result, additional results 120 were obtained for approximately one more hour. During this time, no detectable levels of radiolytically generated particles were detected. At approximately the 3400-second mark of this test, the two HEPA filters 74 were removed from the system, which caused an increase 122 in the detected particles.

Because the particle production decayed to an undetectable level, it is believed that the particles detected for the second flow rate result 110 were the result of the attenuated soft x-rays reacting with residue and/or contaminants left behind on the exposed surfaces of the aerosol conditioning chamber 44 during previous experiments. After the aerosol conditioning chamber 44 was effectively cleansed of these effects, the attenuated soft x-rays no longer generated a detectable level of particles. Accordingly, the detected particles of the second flow rate result 110 are not believed to have been the result of an interaction between the attenuated soft x-rays and the clean air flow 75.

Furthermore, it is noted that the particle increase at the end of the second flow rate result 120 is believed to have nothing to do with radiolytically generated particles. Rather, these are particles that entered the condensation particle counter 78 from ambient by virtue of the attenuated soft x-ray neutralizer 40 being unfiltered. The purpose of the removal of the filters 74 was to verify that the condensation particle counter 78 was still operating.

Accordingly, the attenuated configuration reduced the production of radiolytically generated particles associated with the low flow rate condition to an acceptable or insignificant level, whereas the concentration of radiolytically generated particles produced by the unattenuated configuration at the low flow rate was significant and generally unacceptable.

The descriptors "high flow rate" and "low flow rate" describes only the flow rates as they relate to each other, and are not intended to indicate or imply a limitation of the invention. Also, the level of radiolytically generated particles deemed "insignificant" or "acceptable" depends on the application. For example, in a Class 1 clean room environment used in semiconductor manufacture, the production of radiolytically generated particles may need to be less than $10^{-4}$ particles/cc, whereas in the monitoring of urban atmospheric aerosols a production of radiolytically generated particles of 1 particles/cc may be satisfactory.

Having demonstrated that the attenuated configuration substantially reduces the production of radiolytically generated particles over the unattenuated configuration, a remaining question is whether the attenuated SXRN is effective for the task of conditioning the aerosol. A test was devised and executed to determine the effectiveness of the attenuated configuration, described below.

Figure 7:
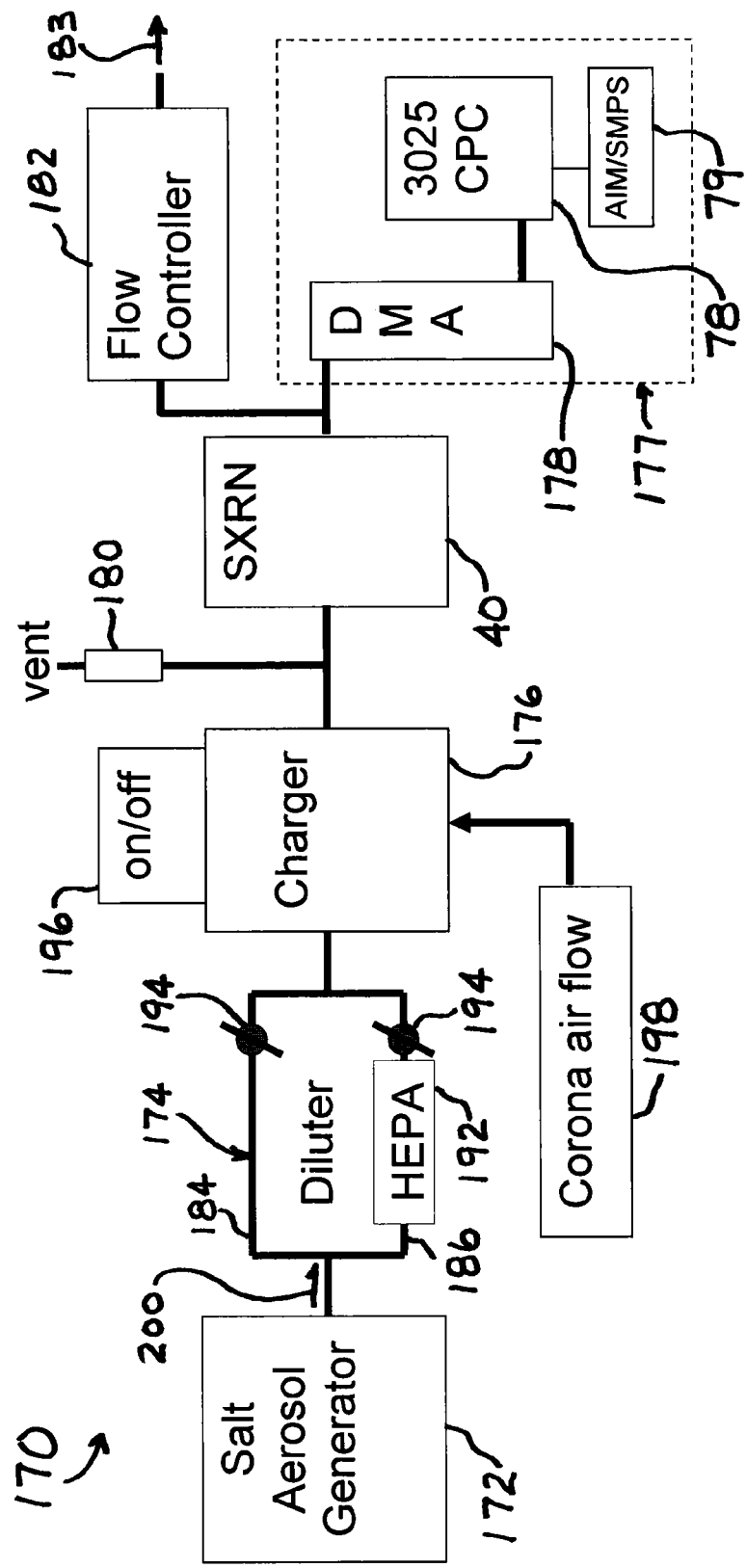
FIG. 7 is a block diagram of a conditioning test setup.
Figure 8:
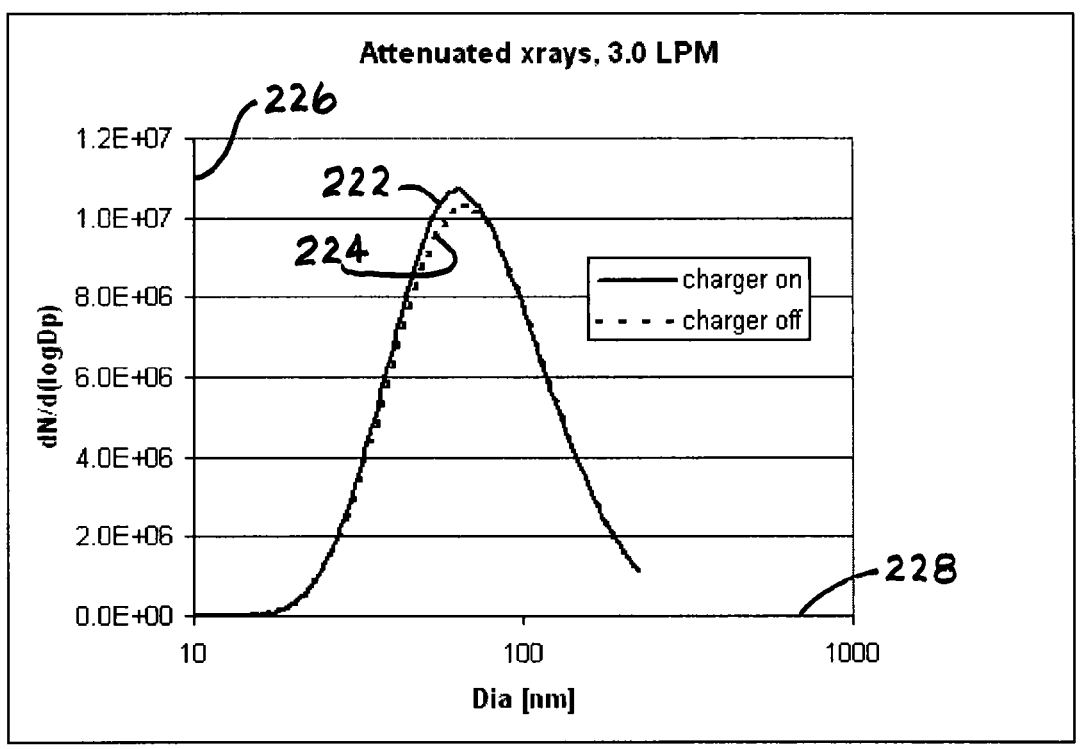
FIG. 8 is a normalized particle distribution of the results of the conditioning test.

Referring to FIG. 7, a conditioning test setup 170 is depicted to test the attenuated configuration of the soft x-ray neutralizer 40 of the invention. The conditioning test setup 170 included a salt aerosol generator 172, a diluter 174, a particle charger 176, the soft x-ray neutralizer 40 in the attenuated configuration, and a scanning mobility particle sizer 177 comprising a differential mobility analyzer (DMA) 178 and the condensation particle counter 78, all in serial fluid communication with each other as depicted in FIG. 7. A vent 180 was located between the particle charger 176 and the soft x-ray neutralizer 40. Also, a flow controller 182 was operatively coupled between the soft x-ray neutralizer 40 and the scanning mobility particle sizer 177.

The diluter 174 included a first flow path 184 and a second flow path 186, the flow paths 184 and 186 being in parallel with each other, the second flow path 186 including a high efficiency particulate air (HEPA) filter 192. The diluter 174 further included a pair of valves 194, one for each of the flow paths 184 and 186.

The particle charger 176 was a unipolar corona-jet charger obtained from a TSI Model 3070A electrical aerosol detector, and included an on/off control 196. The particle charger 176 was set up to accept a regulated clean air flow 198 for the corona air flow. The clean air flow 198 was passed through the particle charger 176 at a rate of approximately 0.4 LPM for this work.

In operation, the salt aerosol generator 172 produced 3.5 liter/minute of aerosol 200 that passed through the diluter 174 and comprising particles of salt. The valves 194 on the diluter could be adjusted to route more or less aerosol through the HEPA filter 192, thus reducing or increasing, respectively, the concentration of the aerosol 200 being passed on for testing. The net flow through the soft x-ray neutralizer 40 was controlled as the sum of the fixed flow through the scanning mobility particle sizer 177 and the adjustable flow through the flow controller 182. The vent 180 provided a path for escape of excess test aerosol flow from the charger 176.

The particle charger 176 could either be in an active state (i.e. controller 196 on) or an inactive state (i.e. controller 196 off). When in the active state, the particle charger 176 imposes a charge on the aerosol 200 as it enters the attenuated soft x-ray neutralizer 40. When in the inactive state, the particle charger 176 is a pass-through device that does not substantially alter the charge distribution of the aerosol 200 as it enters the attenuated soft x-ray neutralizer 40.

The purpose of the DMA 178 was to provide a variable filter that passes particles of a given mobility determined by the voltage setting of the DMA 178. In operation this voltage is scanned while the CPC 78 measures the concentration of particles passing through the DMA 178. The result is a mobility distribution measurement (often interpreted as a size distribution measurement).

Two tests were conducted with the conditioning test setup 170, both with the flow rate through the attenuated soft x-ray neutralizer 40 being set at 3.0 LPM by drawing 1.5 LPM through the scanning mobility particle sizer 177 and an additional 1.5 LPM through the flow controller 182. The higher flow rate was chosen because the shortened residence time in the aerosol conditioning chamber 44 subjects the aerosol to less bombardment of soft x-rays, thus posing a greater challenge to produce a conditioned exit flow.

The first test was conducted with the particle charger 176 in an active state. The second test was conducted with the particle charger 176 in an inactive state. Accordingly, the aerosol entering the attenuated soft x-ray analyzer 40 would be highly charged when the particle charger 176 was activated, and would be representative of an ambient or natural charge when the particle charger 176 was in an inactive state.

Referring to FIG. 8, a particle distribution 220 is presented including the results from the active state test 222 and the results from the inactive state test 224. The particle distribution 220 presents a normalized number concentration of an aerosol 226 (dN/dlogDp, in units of counts/cc per log diameter range) vs. the mobility diameter 228 of the particles within the aerosol.

The dN/dlogDp parameter (hereinafter "normalized number concentration") comprises the number of particles or droplets contained within a mobility diameter interval normalized against the size or "bin width" of the interval. The normalization enables comparison of distributions having different bin widths. To count the total number of particles within a size range, one adds the normalized number concentrations within the size range and multiplies it by the dlogDp (bin width). Here, "dlogDp" or "bin width" is defined as the difference between the base-10 logarithm of the upper limit of the interval and the base-10 logarithm of the lower limit of the interval (i.e. the "bin width" is the base-10 logarithm of the ratio of the upper limit to the lower limit of the interval).

The software 79 of the scanning mobility particle sizer 177 is programmed with certain assumptions in inferring the concentration of particles within a given bin width from a measured particle count. The assumptions include a Fuchs charge distribution for the particles. When the particle charger 176 is in the active state, the actual charge distribution of the particles entering the attenuated soft x-ray neutralizer 40 violates this assumption. Therefore, if the attenuated soft x-ray neutralizer 40 is not conditioning the charged aerosol sufficiently to attain the Fuchs condition, a substantial difference between the two tests 222 and 224 would be observed.

Instead, the results from the two tests 222 and 224 are in close agreement with each other. Such a result implies that the attenuated soft x-ray neutralizer 40 is adequately conditioning the aerosol, regardless of its charged state upon entering the neutralizer 40.

Another way to reduce the intensity of the x-rays entering the aerosol conditioning chamber 44 is to manipulate the operating conditions of the x-ray tube. The x-ray energy or wavelength spectrum is determined by the cathode-to-target voltage, together with the material of the target. The x-ray intensity is established by the current of electrons bombarding the target. The current of electrons is determined by the cathode emission which may be controlled either by changing the cathode temperature (e.g. changing the voltage applied to the cathode or the cathode heater), or through the use of additional control electrodes or grids within the tube. Such control of the cathode emission may provide an alternative or additional way to reduce the intensity of the x-rays from the soft x-ray emitter 42.

It is noted that x-ray tubes have a limited lifetime, and one of the failure mechanisms is growth of crystals resulting in failure of the heated filament in the tube. Operation at full filament temperature tends to inhibit or slow the crystallization process. The acceleration voltage must typically be maintained in order to get the required x-ray spectrum, and with the full acceleration voltage applied and the filament at full temperature, operation at full current and power results. Thus, while it is possible to reduce the x-ray intensity by reducing the filament temperature, this approach is generally not favored because it reduces tube life. The use of control electrodes may be preferable to reducing filament temperature, but it may not be possible without redesign of the x-ray tube itself.

Each of the additional figures and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A method for configuring a device to neutralize an aerosol while generating an insignificant amount of radiolytically generated particles, comprising:

providing a soft x-ray emitter operatively coupled with an aerosol conditioning chamber defining an interior flow passage, said soft x-ray emitter being configured to produce soft x-rays of a rated intensity;

causing said x-ray emitter to emit soft x-rays;

reducing the intensity of at least a portion said soft x-rays produced by said soft x-ray emitter to provide soft x-rays of a reduced intensity relative to said rated intensity;

causing at least a portion of said soft x-rays of said reduced intensity to enter said aerosol conditioning chamber;

causing said aerosol to pass through said conditioning chamber;

bombarding said aerosol with said soft x-rays of said reduced intensity as said aerosol passes through said conditioning chamber;

determining that said soft x-rays of said reduced intensity adequately condition said aerosol; and determining that said soft x-rays of said reduced intensity do not produce radiolytically generated particles above a predetermined amount.

2. The method of claim 1, wherein said step of providing includes providing an attenuating window disposed between said soft x-ray emitter and said interior flow passage of said aerosol conditioning chamber, said attenuating window reducing said at least said portion of soft x-rays to said reduced intensity in said step of reducing.

3. The method of claim 2 wherein said attenuating window in said step of providing causes said reduced intensity to be approximately 33 times less than said rated intensity.

4. The method of claim 2 wherein said reduced intensity is approximately 0.045 Sievert/hour or less.

5. The method of claim 1 wherein said insignificant number of radiolytically generated particles is approximately 1 particles/cc or less.

6. The method of claim 5 wherein said insignificant number of radiolytically generated particles is approximately $10^{-4}$ articles/cc or less.

7. An aerosol conditioning device, comprising:

an aerosol conditioning chamber having an inlet and an outlet and defining an interior flow passage;

a soft x-ray emitter operatively coupled with said aerosol conditioning chamber; and an attenuating window disposed between said soft x-ray emitter and said interior flow passage, said attenuating window being adapted to reduce the intensity of soft x-rays emitted by said soft x-ray emitter and passing through said attenuating window so that radiolytically generated particles produced by said soft x-rays within an aerosol passing through said aerosol conditioning chamber are below a predetermined amount, said aerosol being adequately conditioned by said soft x-rays of reduced intensity.

8. The aerosol conditioning device of claim 7 wherein said attenuating window is configured to reduce the intensity of soft x-rays emitted by said soft x-ray emitter by a factor of approximately 33.

9. The aerosol conditioning device of claim 7 wherein said soft x-rays entering said aerosol conditioning chamber produce an x-ray intensity of approximately 0.045 Sievert/hour or less.

10. The aerosol conditioning device of claim 1 wherein said predetermined amount is a particle concentration.

11. The aerosol conditioning device of claim 7 wherein said predetermined amount is a particle concentration.

12. A method for determining the population of particles in an aerosol while generating no more than an acceptable amount of radiolytically generated particles within said population of particles in said aerosol, comprising:

providing a soft x-ray emitter operatively coupled with an aerosol conditioning chamber that defines an interior flow passage, said soft x-ray emitter being configured to produce soft x-rays of a rated intensity;

establishing a measurable criterion of a desired conditioned aerosol, said conditioned aerosol having a substantially steady state charge distribution, said measurable criterion relating to a sample portion of said population of particles within said conditioned aerosol, said measurable criterion of said desired conditioned aerosol being proportional to $X^N$, where X is an intensity of exposure to soft x-rays and N is a power;

establishing a measurable criterion of said radiolytically generated particles and determining an acceptable level of radiolytically generated particles within said population of particles in said aerosol, said measurable criterion of said radiolytically generated particles being proportional to $X^M$, where M is a power greater than unity and is greater than N;

introducing said aerosol into said interior flow passage of said aerosol conditioning chamber;

operating said x-ray emitter to emit soft x-rays;

causing at least a portion of said soft x-rays emitted by said x-ray emitter to enter said aerosol conditioning chamber at a level of intensity that provides a conditioned aerosol having a criterion within said measurable criterion of said desired conditioned aerosol and provides said acceptable level of radiolytically generated particles; and inferring a population of particles of said aerosol from the measurement of said sample portion of particles in said conditioned aerosol.

13. The method of claim 12 wherein N is not less than ½.

14. The method of claim 12 wherein N is not greater than unity.

15. The method of claim 12 wherein said measurable criterion of said desired conditioned aerosol is indicative of a bipolar population characteristic.

16. The method of claim 12 wherein said level of intensity of said soft x-rays entering said aerosol conditioning chamber in said step of causing is established by attenuation of said soft x-rays.

17. The method of claim 16 wherein said attenuation of said soft x-rays causes said level of intensity of said soft x-rays to be attenuated by a factor of approximately 33 or greater.

18. The method of claim 16 wherein said level of intensity of said soft x-rays entering said aerosol conditioning chamber is approximately 0.045 Sievert/hour or less.

19. The method of claim 12 wherein said acceptable level of radiolytically generated particles is approximately 1 particles/cc or less.

20. The method of claim 19 wherein said acceptable level of radiolytically generated particles is approximately $10^{-4}$ particles/cc or less.

* * * * *